(12) United States Patent
Schrage

(10) Patent No.: US 8,697,756 B2
(45) Date of Patent: Apr. 15, 2014

(54) DIMER DIOL COMPOSITIONS AS SUBSTITUTES OF BODY FLUIDS

(75) Inventor: Norbert Schrage, Aachen (DE)

(73) Assignee: ACTO e.V., Aachen (DE)

( * ) Notice: Subject to any disclaimer, the term of this patent is extended or adjusted under 35 U.S.C. 154(b) by 0 days.

(21) Appl. No.: 13/545,089

(22) Filed: Jul. 10, 2012

(65) Prior Publication Data

US 2014/0018333 A1 Jan. 16, 2014

(51) Int. Cl.
*A61K 47/00* (2006.01)

(52) U.S. Cl.
USPC ................................. 514/772.2; 514/915

(58) Field of Classification Search
None
See application file for complete search history.

(56) References Cited

U.S. PATENT DOCUMENTS

| | | | |
|---|---|---|---|
| 5,258,412 A | 11/1993 | Peyman et al. | |
| 5,795,949 A | 8/1998 | Daute et al. | |
| 5,811,446 A | 9/1998 | Thomas | |
| 2001/0018424 A1 | 8/2001 | Milius et al. | |

FOREIGN PATENT DOCUMENTS

| | | |
|---|---|---|
| DE | 43 08 100 A1 | 9/1994 |
| DE | 195 07 203 A1 | 9/1996 |
| EP | 1 471 898 B1 | 1/2008 |
| WO | 95/34592 A1 | 12/1995 |
| WO | 98/47366 A1 | 10/1998 |

OTHER PUBLICATIONS

Soman, N. and Banerjee, R. Artificial vitreous replacements, 2003, Bio-Medical Materials and Engineering, 13, pp. 59-74.*
Baino, F. Torwards an ideal biomaterial for vitreous replacement: Historical overview and future trends, 2011, Acta Biomaterialia, 7, pp. 921-935.*
Barbucci, R. et al., Hyaluronic acid hydrogel added with ibuprofen-lysine for the local treatment of chondral lesions in the knee: in vitro and in vivo investigations., Oct. 2005, Journal of Biomedical Materials Research. Part B, Applied Biomaterials, 75(1), pp. 42-48.*
Shekarriz, B. et al., Outcome of Palliative Urinary Diversion in the Treatment of Advanced Malignancies, Feb. 15, 1999, Cancer, vol. 85, No. 4, pp. 998-1003.*
European Search Report, dated Mar. 18, 2011, from corresponding European application.
Satish G. Bodige et al., "Structure of an unusual cage dimer diol", Journal of Chemical Crystallography, 1999, pp. 1261-1263, vol. 29, No. 12, XP-002619721; European Search Report.
Saitoh et al., "Long-term effect on optic nerve of silicone oil tamponade in rabbits: histological and EDXA findings", Eye, vol. 16. pp. 171-176, 2002.
Hill, "Fats and oils as oleochemical raw materials", Pure Appl. Chem., vol. 72, No. 7, pp. 1255-1264, 2000.
Agrawal et al., "Silicone Oil-associated Optic Nerve Degeneration", American Journal of Ophthalmology, vol. 133, No. 3, pp. 429-430, Mar. 2002.

* cited by examiner

*Primary Examiner* — Jeffrey S. Lundgren
*Assistant Examiner* — Tori M Strong
(74) *Attorney, Agent, or Firm* — Young & Thompson

(57) ABSTRACT

The invention relates to compositions containing at least 90% by weight of dimer diol for use in a method for the surgical or therapeutic treatment of the human or animal body, and in particular to the use thereof as a body fluid replacement substance.

12 Claims, 5 Drawing Sheets

Determination of vitality
ARPE in direct contact with
dimer diol

Determination of vitality
ARPE cells in direct contact with
medium

Determination of morphology
ARPE cells in direct contact
dimer diol

Determination of morphology
ARPE cells in direct contact with
medium

DIMER DIOL COMPOSITIONS AS SUBSTITUTES OF BODY FLUIDS

FIELD OF THE INVENTION

The present invention relates to compositions containing at least 90% by weight of dimer diol for use in a method for the surgical or therapeutic treatment of the human or animal body.

BACKGROUND OF THE INVENTION

The replacement of body fluids in the region of mucous membranes and internal cavities of the body which are coated with mucous membrane or epithelial cells (apart from blood vessels) is at present a typical application for aqueous liquids such as for example tear-replacement substances in the lachrymal ducts or artificial saliva in the region of the oral cavity, but also for silicone oil or fluorocarbon liquids which are used as endotamponades in the region of the vitreous body of the eye (as described for example in U.S. Pat. No. 5,258,412).

The special feature of the human or animal body surface is that aqueous liquids are subject to an extensive exchange of substances there as a rule and thus usually remain for an undesirably short time on the body surface. In contrast, oils, such as for example silicone oils, are provided as a rule as surface therapeutic agents which remain for a long time. Intraocular tamponades (endotamponades) based on silicone oil are even agents which remain permanently or which have to be removed after some time.

Oils, then, are generally used in medicine when a high interfacial tension and a low interaction with the aqueous systems of the body are desired. Oils are broken down only with the addition of emulsifiers or specific enzyme systems. A natural breaking down of silicone oil is not possible since the body has no suitable enzyme system for splitting the molecules. Low-molecular portions of the silicone oil are suspected, however, of being a cause of certain degenerative processes in the body. In this way, damage to the neuronal apparatus of the retina are attributed to them for example when used as a vitreous body replacement substance (Saitoh et al., Long-term effect on optic nerve of silicone oil tamponade in rabbits: histological and EDXA findings. *Eye*, 2002, 16(2):171-176; Agrawal et al., Silicone oil-associated optic nerve degeneration. *Am. J. Ophthalmol.*, 2002 133(3):429-430).

Other bio-compatible substances with high surface tension and little tendency to foam formation (emulsification) are therefore in principle attractive candidates for the replacement of vitreous bodies, tears and for the non-aqueous treatment of skin and mucous membranes.

In the scope of his research work the Applicant has established that a specific substance which is already known per se and is like oil but not like silicone oil is excellently suitable as a body replacement substance and can be used for example as an artificial tear substance or as an artificial vitreous body without any drawbacks.

This substance already known per se and on the market is dimer diol. In the present application dimer diols are understood to be predominantly products containing aliphatic or cycloaliphatic bivalent alcohols which are generally obtained by the dimerization of unsaturated fatty acids and the subsequent reduction of the acid groups to form hydroxyl groups. Dimer diols of this type have been in widespread use for decades, for example in the form of monomers for the production of plastics, in particular of polyurethanes (see for example DE 43 08 100, WO 95/34592).

Dimer diols are likewise already known in cosmetic and pharmaceutical compositions, where they are used, however, only in small portions which do not exceed approximately 20% (see for example EP 1 471 898, DE 195 07 203, US 2001/0018424 and WO 98/47366).

To the best of the Applicant's knowledge, however, dimer diols in a relatively pure form have until now never been considered for medical use. The Applicant has tested dimer diols for their bio-compatibility and has found that these substances have an excellent compatibility on the surface of the eye as well as in contact with the nerve fibre layer of the inside of the eye. Dimer diol can therefore advantageously replace the silicone oils used until now.

Dimer diols are clearly transparent and do not mix with water. They are suitable for producing a lipid layer of high surface tension on the surface of the eye and in the interior of the eye as well as on any other mucous membrane and body cavity. In this way, these substances are excellently suitable for stabilizing and packing sensitive surfaces on account of the high surface tension, as is necessary in the case of an internal splinting of the retina by a vitreous body replacement substance.

BRIEF SUMMARY OF THE INVENTION

A first subject of the invention is therefore a composition containing at least 90% by weight, preferably at least 95% by weight and ideally at least 98% by weight of dimer diol for use in a method for the surgical or therapeutic treatment of the human or animal body.

As has already been made clear in the introduction, these compositions are not novel per se, since dimer diols have already been used in an almost pure form in non-medical fields.

Pharmaceuticals which have a high proportion, i.e. a proportion of at least 90% by weight, of dimer diols are, to the best of the Applicant's knowledge, nevertheless not yet known and the present invention therefore likewise has as its subject matter a sterile and sterile-packed composition which contains at least 90% by weight of dimer diol and which, in addition, contains at least one pharmaceutical active substance.

DETAILED DESCRIPTION OF THE INVENTION

Within the scope of this therapeutic or surgical treatment the compositions of the invention are preferably selected as a body fluid replacement substance from the group comprising artificial tears, artificial mucus and endotamponades.

The pharmaceutical active substances contained in the mixtures of substances according to the invention are preferably selected from the group comprising fat-soluble vitamins, steroids, antibiotics and immunomodulatory active substances. These pharmaceutical active substances are advantageously soluble and dissolved in the dimer diol compositions, in particular in applications where good transparency is important. The compositions according to the invention advantageously contain altogether approximately 0.01% to 1%, preferably between 0.1 [and] 0.5%, of at least one pharmaceutical active substance.

The dimer diol compositions can be applied to the surface of the eye or can be introduced into the lachrymal sac, for example for the treatment of xerophthalmia, of states of burning and irritation of the eye, of Lyell's syndrome, of *Pemphigus vulgaris*, of ocular pemphigoid, of inflammation of the cornea, of ulcers of the cornea and of erosions of the cornea.

They can likewise be applied to the nasal mucous membrane in order to treat affection and inflammation of nasal mucous membranes.

Within the scope of the use as an endotamponade the dimer diol compositions are useful both in body cavities with an epithelial lining and in body cavities without an epithelial lining.

The vitreous body space is a body cavity without an epithelial lining and the dimer diol compositions can be used there for example as an endotamponade for the treatment of detachment of the retina, of proliferative vitreoretinopathy, of glaucoma, of uveitis, of inflammation of the optic nerve and for the long-term treatment of inflammatory retinal diseases.

By way of example, endotamponades of body cavities provided with an epithelial lining which may be named are gall bladder tamponades, bladder tamponades and intestine tamponades, which are used for the treatment of inflammatory or post-operative irritation of the corresponding body cavities.

As already mentioned in the introduction, the dimer diols used according to the invention, also known as dimeric alcohols, are mixtures which predominantly contain aliphatic or cycloaliphatic bivalent alcohols and which can be obtained by reduction of dimeric fatty acids. Dimeric fatty acids are in turn prepared by the dimerization of unsaturated fatty acids.

Figure 5:
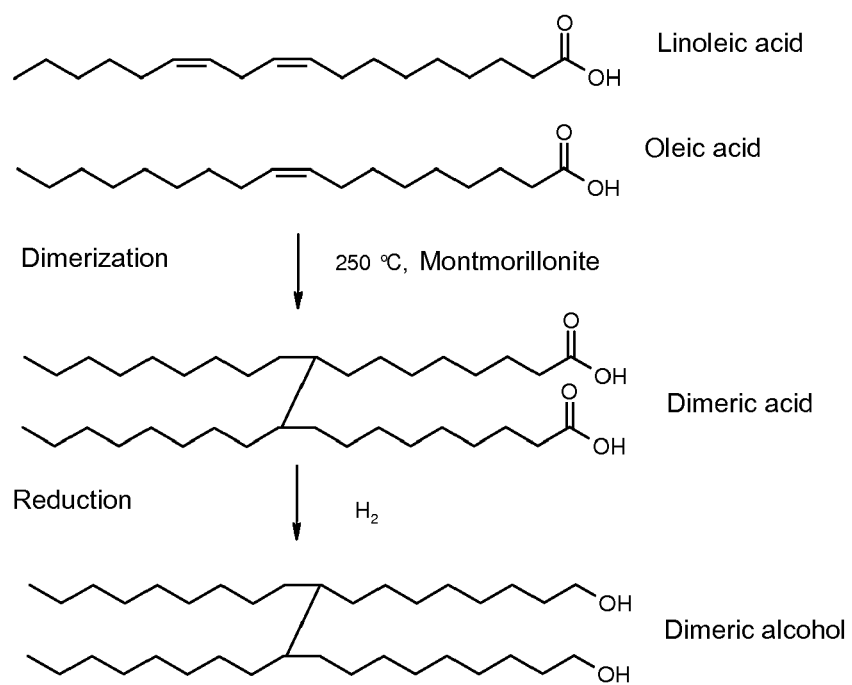
FIG. 5 shows the synthesis of a C36 dimer diol starting from linoleic acid and oleic acid.

The highly simplified diagram reproduced in FIG. 5 (Karlheinz Hill, *Pure Appl. Chem.*, Vol. 72, No. 7, pp. 1255 to 1264, 2000) shows the synthesis of a C36 dimer diol starting from linoleic acid and oleic acid.

Dimeric alcohols generally contain a certain portion of monomers and trimers resulting from the synthesis. In the compositions according to the invention this portion is as a whole less than 10%, preferably less than 8% weight, in a particularly preferred manner less than 5%, and ideally less than 3%, relative to the sum of monomers, dimers (dimer diols) and trimers. These percentages are, like all other percentages of this application, to be understood as being percentages by weight.

As already mentioned in the introduction, the dimer diols used according to the invention must naturally both be sterile and be packed in a sterile manner for the intended use as body fluid replacement substances. The sterilization can be carried out in a manner known to the person skilled in the art, for example by sterile filtration, irradiation with gamma rays or heating, for example for approximately an hour at 130° C.

The sterile packing can likewise be carried out in a manner known to the person skilled in the art. Suitable containers are for example vials, in particular eye drop vials, ampoules, pre-filled syringes or bags.

Figure 1:
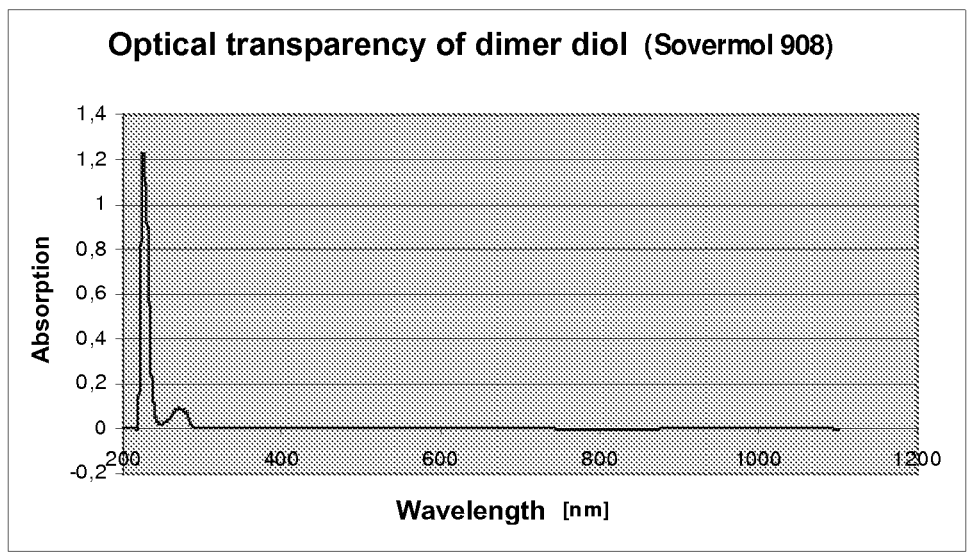
FIG. 1 shows the absorption spectrum of a dimer diol capable of being used satisfactorily for the invention (Sovermol 908, Cognis Deutschland GmbH).

The dimer diols used according to the invention and the pharmaceutical compositions according to the invention should be as transparent as possible, in particular if they are used as a vitreous body replacement substance. FIG. 1 shows the absorption spectrum of a dimer diol capable of being used satisfactorily for the invention (Sovermol 908, Cognis Deutschland GmbH). It will be noted that this product is completely transparent in the entire visible and infrared range.

The dimer diols used according to the invention should not be too runny, in particular in the application as a vitreous body replacement substance, as they would otherwise not provide an adequate hold for the eye. On the other hand their viscosity should not be so high that their dropping or injection ability could be impaired.

The dimer diols preferably have a Brookfield viscosity—determined according to ISO 2555 with a Rheotec RC02 rotation viscosimeter at 25° C.—of approximately from 1500 to 3200 mPa·s, in a particularly preferred manner of approximately from 1800 to 2800 mPa·s.

As already mentioned in the introduction, dimer diols provide the advantage of a relatively high surface tension. This generally amounts to at least 30 mN/m (measured in accordance with the Wilhelmy plate method), preferably at least 35 mN/m. This high surface tension is extremely important if the dimer diols are used as an endotamponade, in particular as a vitreous body replacement substance. It ensures in fact that the dimer diol composition does not emulsify in the course of time with the aqueous body fluid from the immediate surroundings of the vitreous body, which would inevitably lead to an unacceptable degree of turbidity.

As well as the properties named in the foregoing (transparency, viscosity, surface tension), the dimer diols used according to the invention must naturally be completely bio-compatible and should not be cytotoxic.

Figure 2:
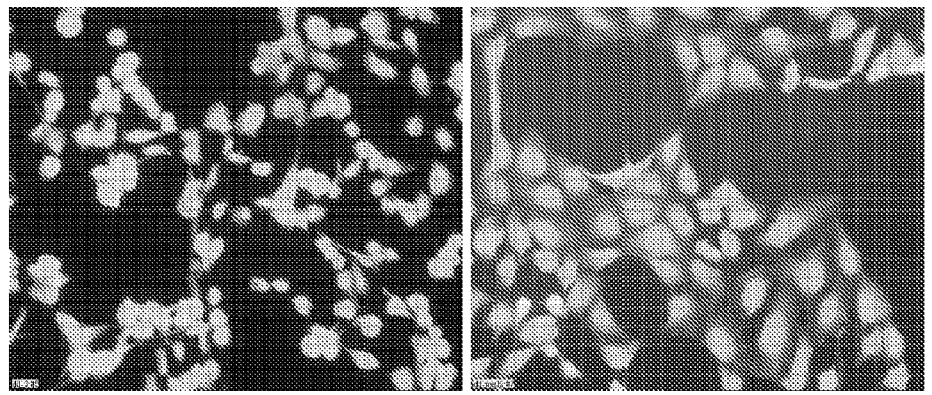
FIG. 2 shows the vitality and morphology of adult retinal pigment epithelial cells (ARPE cells) in culture in direct contact with a dimer diol which is commercially available and preferred according to the invention (Sovermol 908, Cognis Deutschland GmbH) for a duration of 24 hours in comparison with a culture on a conventional culture medium (MEM and Serum FCS 10%).
Figure 2:
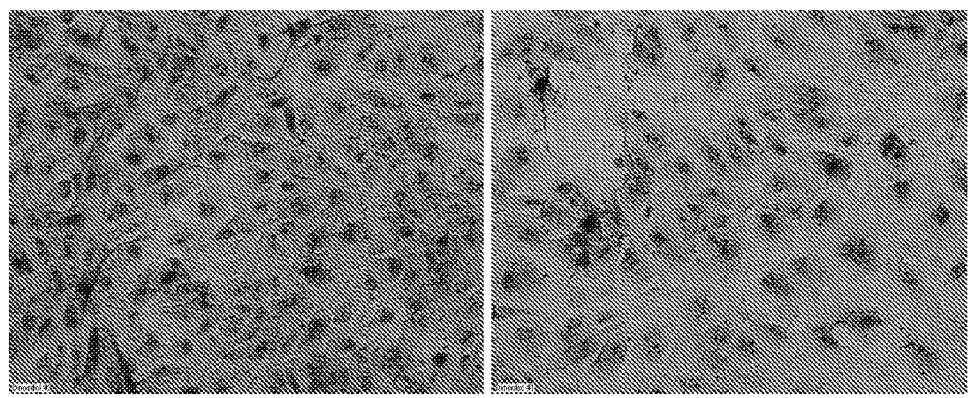

The Applicant has put adult retinal pigment epithelial cells (ARPE cells) in culture in direct contact with a dimer diol which is commercially available and preferred according to the invention (Sovermol 908, Cognis Deutschland GmbH) for a duration of 24 hours and has then determined the vitality and morphology in comparison with a culture on a conventional culture medium (MEM and Serum FCS 10%). FIG. 2 shows the results of these tests. It will be noted that the epithelial cells in no way suffer in the exchange of the conventional culture medium for the dimer diol. Neither the vitality nor the morphology of the cells after 24 hours on dimer diol is adversely affected.

These different investigations show, therefore, that dimer diols are excellent candidates for body fluid replacement substances.

In another series of tests the Applicant tested the influence of dimer diol upon the healing process of the cornea in an animal experiment. In this case the eye drops HYLO-COMOD® (sterile aqueous solution containing hyaluronic acid and citrate buffer) were used as a positive control. The following Example contains a detailed description of these tests which have shown that dimer diol has a good healing effect of the rabbit cornea comparable with the positive control substance and has no toxicity and is thus a very promising candidate for eye drops or tear replacement substance.

EXAMPLE

Figure 3:
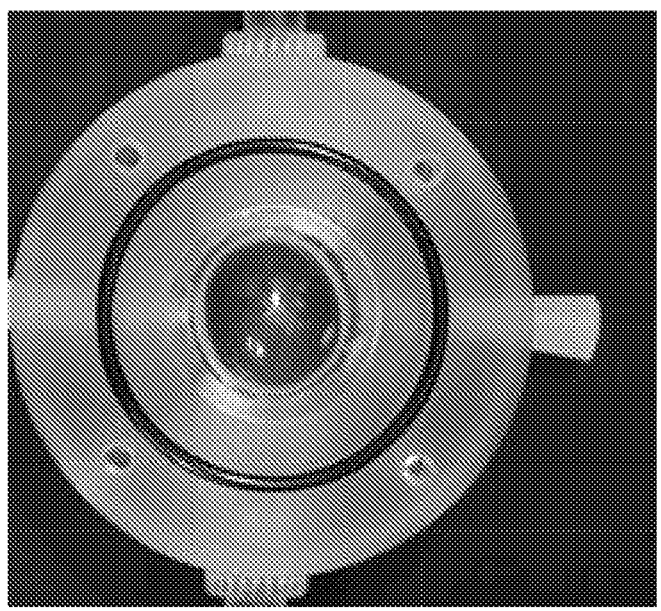
FIG. 3 shows the ex vivo eye irritation test (EVEIT) in which cultivated corneas can be kept alive for days outside the animal.

In the ex vivo eye irritation test (EVEIT) (FIG. 3) cultivated corneas can be kept alive for days outside the animal Small surface changes heal up of course in this system. To this end, the corneas are continuously (6 µl per minute) supplied with MEM nutrient (minimal essential medium without calf serum).

After a stabilization period of twelve hours small erosions were applied in each case to five rabbit corneas for each test. These wounds show up yellow-green under fluorescein coloration in blue light and their healing can therefore be followed closely under the magnifying glass.

On each cornea 200 µl Hylo Comod® eye drops (control) or 200 µl dimer diol (invention) were applied in each case with a central cannula in the centre of the cornea 12 times daily during the day. The corneas were continuously supplied with MEM at night.

Figure 4:
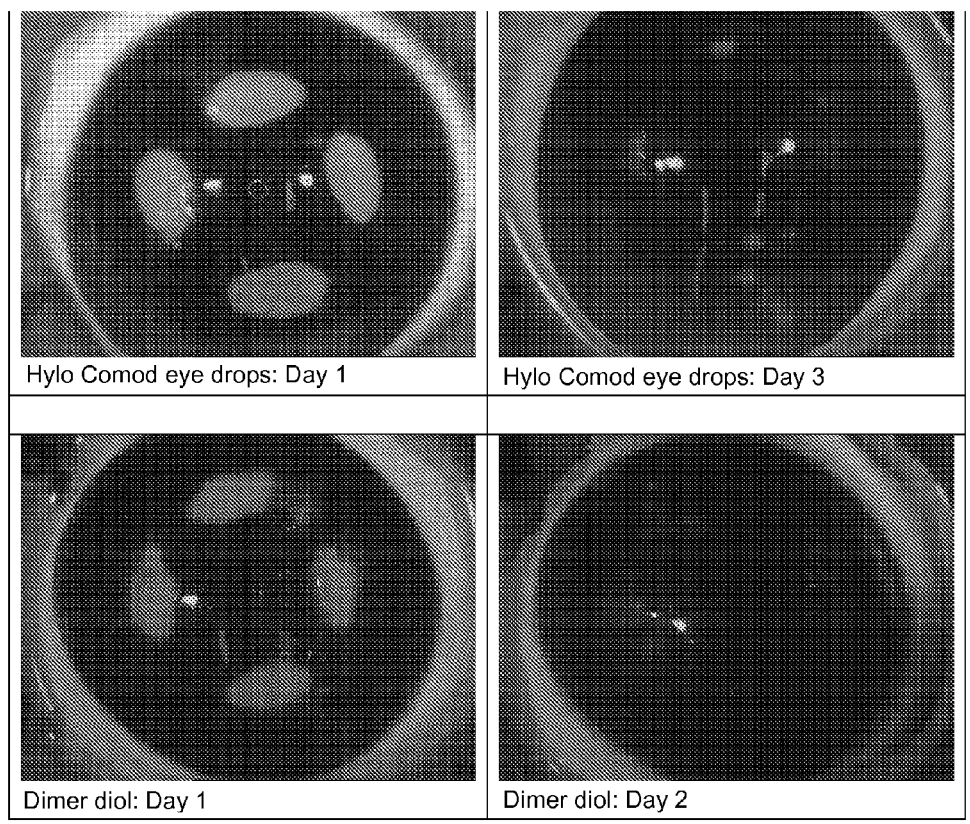
FIG. 4 shows the healing of small erosions applied to rabbit corneas with the known tear replacement substance Hylo Comod® eye drops in comparison with the dimer diol according to the invention.

In only three days almost complete healing takes place with the known tear replacement substance Hylo Comod® eye drops: yellow-green areas become smaller and disappear almost completely. Nevertheless, the surface heals even better with the dimer diol according to the invention. After only two days a wound can no longer be detected (FIG. 4).

The invention claimed is:

1. A method for surgical or therapeutic treatment of a human eye or an animal eye, comprising administering to said human eye or said animal eye an effective amount of a composition containing at least 90% by weight of dimer diol.

2. The method for surgical or therapeutic treatment of a human eye or an animal eye of claim 1, wherein the dimer diol containing composition is comprised in a body fluid replacement substance selected from the group consisting of artificial tears, artificial mucous membrane and endotamponades.

3. The method of claim 2 for treating dryness of the mucous membrane or xerophthalmia in a human eye or an animal eye in need thereof, comprising administering to said human eye or said animal eye an effective amount of the dimer diol containing composition.

4. The method of claim 1 for treating dryness of the mucous membrane or xerophthalmia in a human eye or an animal eye in need thereof, comprising administering to said human eye or said animal eye an effective amount of the dimer diol containing composition.

5. The method of claim 1, wherein the proportion by weight of dimer diol the dimer diol containing composition amounts to at least 95% by weight.

6. The method of claim 1, wherein the dimer diol containing composition has a Brookfield viscosity at 25° C. according to ISO 2555 of from 1500 to 3200 mPa·s.

7. The method of claim 1, wherein the dimer diol containing composition is sterile and is packed, sealed off tightly from the environment, in a container.

8. The method of claim 1, wherein the dimer diol containing composition additionally contains at least one pharmaceutical active substance selected from the group consisting of fat-soluble vitamins, steroids, antibiotics and immunomodulatory active substances.

9. The method of claim 1, wherein the dimer diol containing composition is sterile and sterile-packed and contains at least one pharmaceutical active substance.

10. The method of claim 9, wherein the dimer diol containing composition is selected from the group consisting of fat-soluble vitamins, steroids, antibiotics and immunomodulatory active substances.

11. The method of claim 9, wherein the proportion by weight of dimer diol in the dimer diol containing composition amounts to at least 95% by weight.

12. The method of claim 9, wherein the dimer diol containing composition has a Brookfield viscosity at 25° C. (according to ISO 2555) of from 1500 to 3200 mPa·s.

* * * * *